(12) United States Patent
Ahn

(10) Patent No.: US 11,413,182 B2
(45) Date of Patent: Aug. 16, 2022

(54) CERVICAL BRACE

(71) Applicant: KOREA INSTITUTE OF INDUSTRIAL TECHNOLOGY, Cheonan-si (KR)

(72) Inventor: Bum Mo Ahn, Anyang-si (KR)

(73) Assignee: Korea Institute of Industrial Technology, Cheonan-si (KR)

( * ) Notice: Subject to any disclaimer, the term of this patent is extended or adjusted under 35 U.S.C. 154(b) by 658 days.

(21) Appl. No.: 15/556,423

(22) PCT Filed: Mar. 8, 2016

(86) PCT No.: PCT/KR2016/002289
§ 371 (c)(1),
(2) Date: Sep. 7, 2017

(87) PCT Pub. No.: WO2016/144080
PCT Pub. Date: Sep. 15, 2016

(65) Prior Publication Data
US 2018/0042756 A1 Feb. 15, 2018

(30) Foreign Application Priority Data

Mar. 9, 2015 (KR) .......................... 10-2015-0032621

(51) Int. Cl.
*A61F 5/04* (2006.01)
*A61F 5/05* (2006.01)
*A61F 5/055* (2006.01)

(52) U.S. Cl.
CPC .................... *A61F 5/055* (2013.01)

(58) Field of Classification Search
CPC .. A61F 5/04; A61F 5/048; A61F 5/055; A61F 5/028; A61F 5/042; A61F 5/05883;
(Continued)

(56) References Cited

U.S. PATENT DOCUMENTS

| 305,876 | A | * | 9/1884 | Ainsworth | ................ F16B 7/06 254/233 |
| 3,813,132 | A | * | 5/1974 | Sahm | ...................... F16C 29/02 384/42 |
| 2004/0204666 | A1 | * | 10/2004 | Marsh | ..................... A61F 5/055 602/18 |

FOREIGN PATENT DOCUMENTS

| JP | 07-313539 A | 12/1995 |
| KR | 10-2003-0084494 A | 11/2003 |

(Continued)

OTHER PUBLICATIONS

Espacenet Machine Translation of KR-101205438B1; "KR101205438B1_KR and ENG machine translations.pdf".*

*Primary Examiner* — Rachael E Bredefeld
*Assistant Examiner* — Brant T Bennett
(74) *Attorney, Agent, or Firm* — Rabin & Berdo, P.C.

(57) ABSTRACT

Provided is a cervical brace. The cervical brace according to the present invention may include an upper support that supports and covers a jaw of a wearer, a lower support supported by being pressed against shoulders around the neck of the wearer, a rear support that is positioned behind the upper support and the lower support and supports the rear of the wearer's neck, and a height adjuster including a body installed at one side surface of the upper support, a connecting member formed to extend from one surface of the lower support toward the body, and a rotating member that is installed at one side of the body such that the connecting member penetrates and rotates about the connecting member in both directions, wherein the body of the height adjuster moves upward and downward along the connecting member according to a rotating direction of the rotating member and thus the upper support moves upward and downward with respect to the lower support.

6 Claims, 10 Drawing Sheets

(58) Field of Classification Search
CPC .. A61F 5/05841; A61F 5/05808; A61F 5/026;
A61F 2005/0165; Y10T 24/44017; Y10T
24/44974; F16B 2200/30; F16B 7/06;
F16B 7/025; F16B 7/18; F16B 7/185;
F16B 7/182; F16B 7/187; F16B 13/0808;
F16M 13/02; F16H 25/2015; A61H
1/0296; A61H 1/0218
See application file for complete search history.

(56) References Cited

FOREIGN PATENT DOCUMENTS

| KR | 10-2003-0097470 A | 12/2003 |
| KR | 10-2008-0090821 A | 10/2008 |
| KR | 10-2011-0130300 A | 12/2011 |
| KR | 101205438 B1 * | 11/2012 |

* cited by examiner

CERVICAL BRACE

TECHNICAL FIELD

The present invention relates to a cervical brace.

BACKGROUND ART

Generally, within the spine, the cervical vertebrae include the seven vertebrae which support the skull above the thoracic vertebrae.

Since the cervical vertebrae bend slightly forward from above the thoracic vertebrae, the cervical vertebrae are a portion on which the weight of the skull is borne the most when a person stands, and particularly when a person sits on a chair to work for a long time. Accordingly, the cervical vertebrae may be displaced or depart from a normal position due to incorrect posture, life habits, lack of exercise, and the like. Therefore, intervertebral disks of the cervical vertebrae are pressed, which causes pains and negative symptoms that influence other body parts connected through the nervous system.

Acupressure treatment, massage, acupuncture, moxibustion, and the like are used in oriental medicine, while physical treatment, traction, chiropractic, trans urethral needle ablation (TUNA) treatment, and the like are currently used in hospitals to correct abnormally transformed cervical vertebrae. However, as a result of observation of patients, there were problems in that the oriental treatment, chiropractic, and TUNA treatment normally only soften stiff muscles of the cervical vertebrae and correct a transverse process of the cervical vertebrae, the traction only induces pain by linearly pulling the cervical vertebrae without considering a basic normal state of the cervical vertebrae in which the seven vertebrae bend to extend from the thoracic vertebrae to the cervical vertebrae, the cervical vertebrae that were displaced and departed from their normal position are not corrected to the normal position, and the same problem is repeated.

For example, among parts of the human body, the cervical vertebrae are the vertebrae positioned at the upper end of the spine, i.e., the neck, of which there are seven, and are capable of pivoting, bending and expanding, unlike the lumbar and the thoracic vertebrae.

Conventionally, there are cervical disorders such as whiplash injury, ruptured cervical disk, fracture of cervical spine, spinal stenosis, ossification of a posterior longitudinal ligament, spinal tumor, among which the most common are whiplash injury and ruptured cervical disks.

A symptom of a whiplash injury is that, when surrounding muscles, tendons, or the like supporting the cervical vertebrae are tensed or relaxed abnormally, or the cervical vertebrae are excessively expanded, bent, twisted, pressed against a shaft by an external force, neck muscles and the muscles, tendons, or the like which wrap around the cervical vertebrae are expanded or torn and become swollen and sore.

In addition, a ruptured cervical disk is also referred to as a cervical herniated nucleus and is a disorder that develops due to degenerative changes in cervical disks.

A ruptured cervical disk may develop due to external injury or chronic stimulation, may develop as part of a degenerative disorder due to aging, and may develop acutely when incorrect posture is fixedly maintained for a long time in daily life.

It is preferable that a stiffness or relaxation phenomenon of the cervical muscles corresponding to the above-described cases be treated using a physical treatment method which transfers physical stimulation.

In the case of a patient whose cervical vertebrae are abnormal, it is very important to maintain stable posture of the cervical vertebrae in daily life in addition to a physical treatment. However, in the case of a conventional cervical correction device or cervical protector, there is a problem in that the neck is wrapped up to restrict only movement of the neck.

In addition, a cervical brace according to known art having a gear drive type operated through a knob operation has a problem in that gears are abraded and broken due to load generated when a gap between the gears and a height are adjusted.

DISCLOSURE

Technical Problem

The present invention is directed to providing a cervical brace that is easily and suitably adjusted to a wearer's body shape to improve a wearing sensation.

Technical Solution

One aspect of the present invention provides a cervical brace including an upper support that supports and covers a jaw of a wearer, a lower support supported by being pressed against shoulders around the neck of the wearer, a rear support that is positioned behind the upper support and the lower support and supports the rear of the neck of the wearer, and a height adjuster including a body installed at one side surface of the upper support, a connecting member formed to extend from one surface of the lower support toward the body, and a rotating member that is installed at one side of the body such that the connecting member penetrates and rotates about the connecting member in both directions, wherein the body of the height adjuster moves upward and downward along the connecting member according to a rotating direction of the rotating member and thus the upper support moves upward and downward with respect to the lower support.

The body of the height adjuster may be installed to be detachable from the upper support, and a fixing member to which the body is coupled to be fixed may be installed at the upper support.

An angle adjusting member configured to adjust an angle of the upper support with respect to the jaw of the wearer may be detachably installed at the other side of the body, and the angle adjusting member may be coupled to the fixing member by sliding.

The angle adjusting member may be screwed to the body.

The angle adjusting member may have a section formed in a trapezoidal shape.

The fixing member may have a guide groove formed in a shape corresponding to the angle adjusting member.

The body has an accommodation portion formed to be opened in one direction through which the rotating member is accommodated, and a pair of through holes through which the connecting member penetrates may be formed at upper and lower portions of the accommodation portion.

Coupling members coupled to the connecting member may be disposed at the rotating member through which the connecting member penetrates.

Seating grooves in which the coupling members are seated may be formed in the rotating member at which the coupling members are disposed.

The seating grooves may be formed in one and the other surfaces of the rotating member, and the coupling members may be provided in a pair and respectively seated in the pair of seating grooves formed in one and the other surfaces of the rotating member.

The coupling member may be formed in a nut shape, and the connecting member may have a screw thread formed on a circumferential surface to be coupled to the coupling member.

A support member to which the connecting member is fixed may be installed at one surface of the lower support.

Advantageous Effects

As a cervical brace according to one embodiment of the present invention includes a height adjuster that is connected to one side of an upper support that supports a wearer's jaw and a lower support and adjusts a height of the upper support, and an angle adjusting member, the height and an angle of the upper support can be easily and suitably adjusted to a wearer's body shape. Therefore, a wearing sensation can be improved.

In addition, since a coupling member of the height adjuster is formed in a nut shape, and a connecting member has a screw thread formed on a circumferential surface to be coupled to the coupling member, the number of parts is dramatically decreased. Therefore, the manufacturing and assembly cost of the product can be decreased.

In addition, since the height adjuster and the coupling member are formed in nut shapes, and the connecting member has the screw thread formed on the circumferential surface to be coupled to the coupling member, abrasion phenomena can be prevented.

MODES OF THE INVENTION

Figure 1:
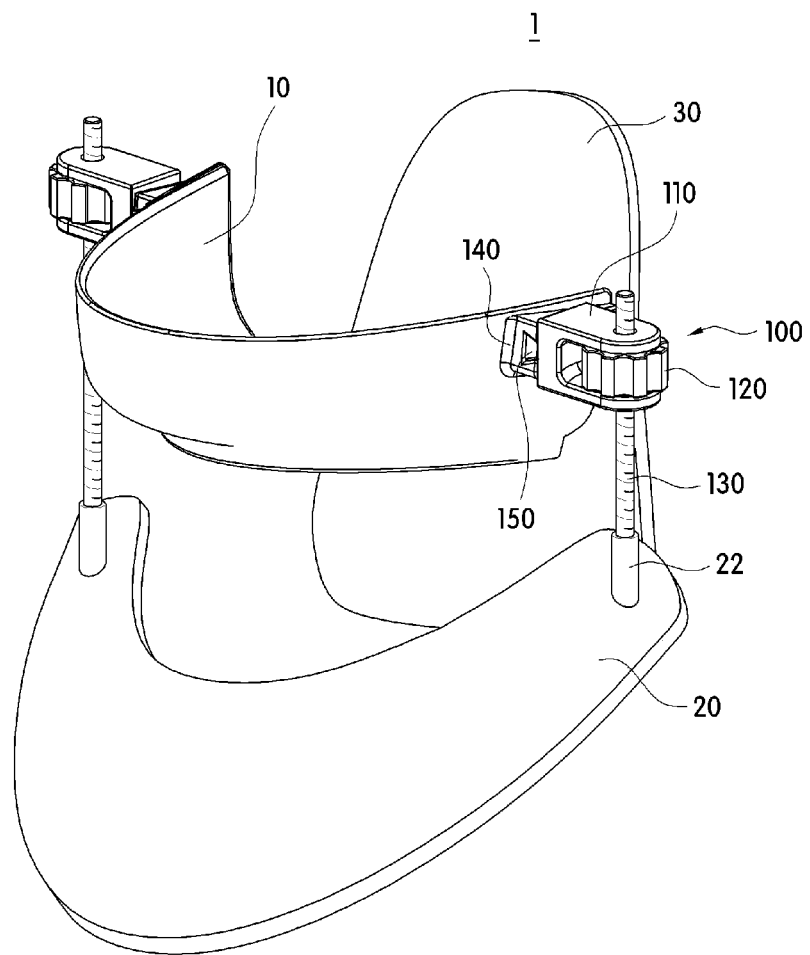
FIG. 1 is a perspective view illustrating a cervical brace according to one embodiment of the present invention.

Hereinafter, embodiments that can be easily performed by those skilled in the art will be described in detail with reference to the accompanying drawings. However, embodiments of the present invention may be implemented in several different forms, and are not limited to embodiments described herein. In addition, parts irrelevant to description are omitted in the drawings in order to clearly explain embodiments of the present invention. Similar parts are denoted by similar reference numerals throughout this specification.

Figure 2:
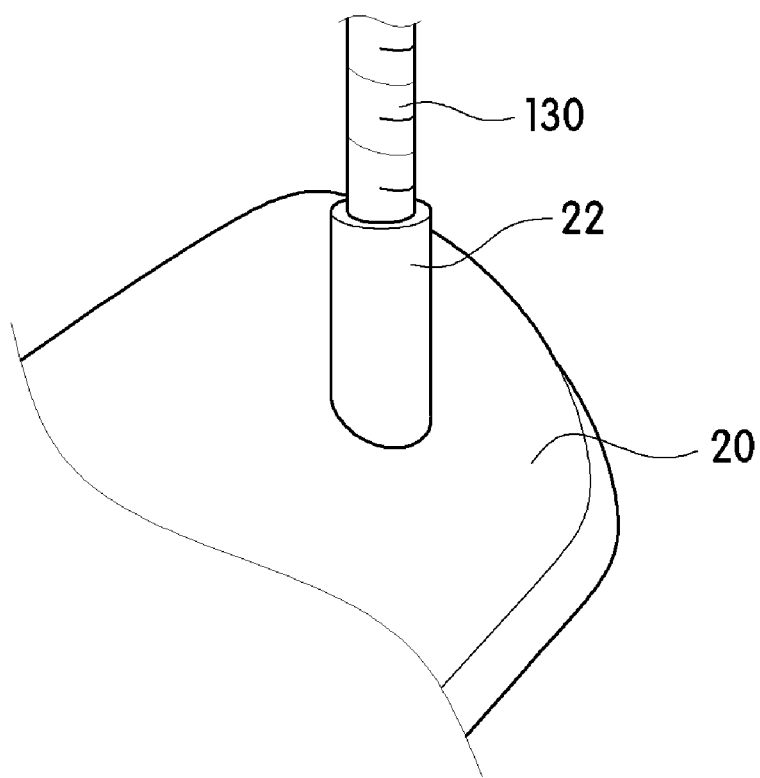
FIG. 2 is a coupling view of a lower support and a support member of the cervical brace according to one embodiment of the present invention.

FIG. 1 is a perspective view illustrating a cervical brace according to one embodiment of the present invention, and FIG. 2 is a coupling view of a lower support and a support member of the cervical brace according to one embodiment of the present invention.

As illustrated in FIG. 1, a cervical brace 1 may include an upper support 10 covering and supporting a wearer's jaw, a lower support 20 that is pressed against and supported by the shoulders around the wearer's neck, a rear support 30 that is positioned behind the upper and lower supports 10 and 20 and supports the rear of the wearer's neck, and height adjusters 100 that perpendicularly move the upper support 10 to the lower support 20.

The upper support 10 supports the wearer's jaw from below. As the upper support 10 presses and supports the wearer's jaw upward, the neck, that is, the cervical vertebrae, may stand correctly.

As the upper support 10 has a curved shape to match the wearer's jawline and the lower outline thereof, the upper support 10 may be pressed against the wearer's entire jaw, and thus may provide a convenient wearing sensation.

In addition, fixing members 140 to which the height adjusters 100 may be detachably coupled may be installed on both sides of the upper support 10.

The fixing members 140 will be described below in detail with reference to FIG. 10.

The lower support 20 serves as a base that supports the overall cervical brace 1, and may be formed with a curved plate in a shape that covers to fit the curvature of the body by extending along the circumference around the wearer's neck to the front, both shoulders, and a partial rear of the shoulders.

The lower support 20 is put on and pressed against the circumference around the neck when worn, and supports the overall cervical brace 1, and since the rear of the lower support 20 is open, the wearer may easily put on and take off the cervical brace 1.

In addition, support members 22 that support connecting members 130 may be formed on one surface of the lower support 2. Specifically, the support members 22 may be installed at one surface of the lower support 20 corresponding to the height adjusters 100.

Here, the support members 22 may be formed in cylindrical shapes as illustrated in FIG. 2. The connecting members 130 of the height adjusters 100 that will be described below may be fixedly coupled to upper portions of the cylindrical support members 22, or the connecting members 130 may be inserted into the support members 22 to be fixedly coupled thereto.

Meanwhile, a coupling structure of the support members 22 and the lower support 20 is not limited to a configuration described as illustrated in FIG. 2. For example, the coupling structure may be freely configured as long as the support members 22 can fixedly couple the connecting portions 130 to the lower support 20.

The rear support 30 supports the rear of the wearer's neck, and may pair with the upper support 10 to hold the entire circumference of the wearer's neck to be balanced.

The height adjusters 100 will be described below with reference to FIGS. 3 to 11.

Figure 3:
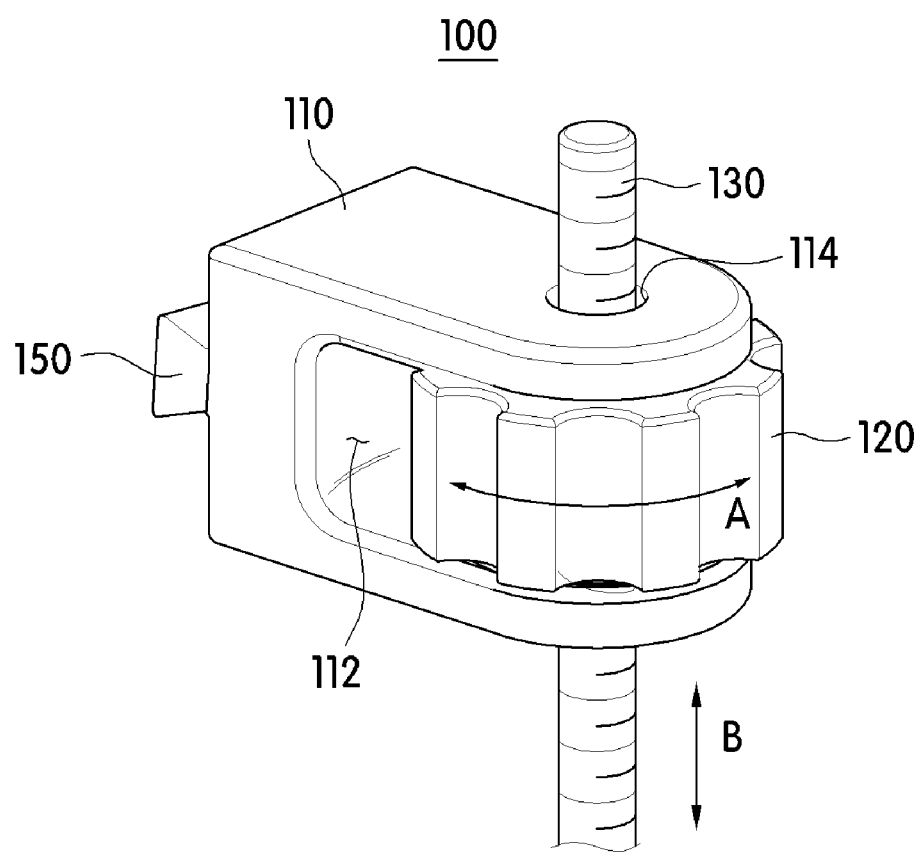
FIG. 3 is a perspective view illustrating a height adjuster of the cervical brace according to one embodiment of the present invention.
Figure 4:
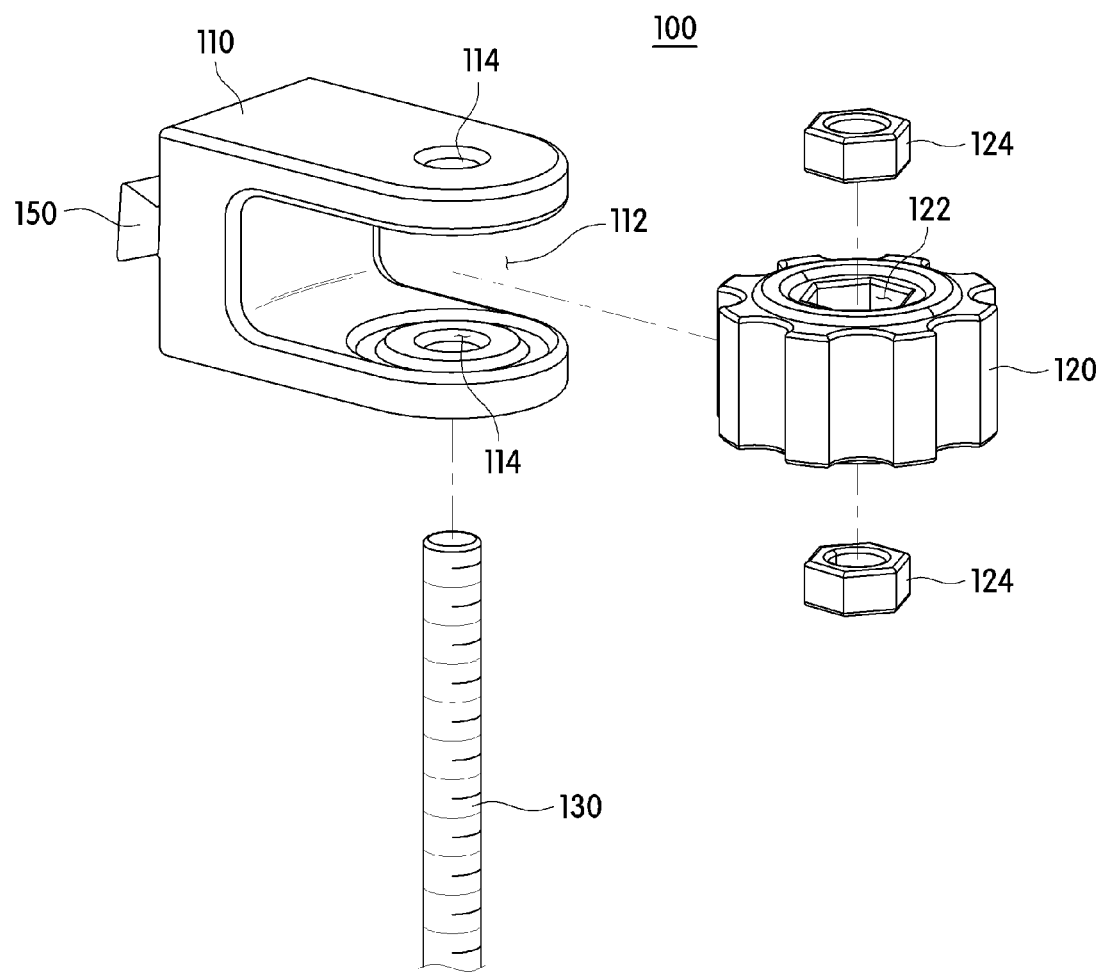
FIG. 4 is an exploded perspective view in FIG. 3.
Figure 5:
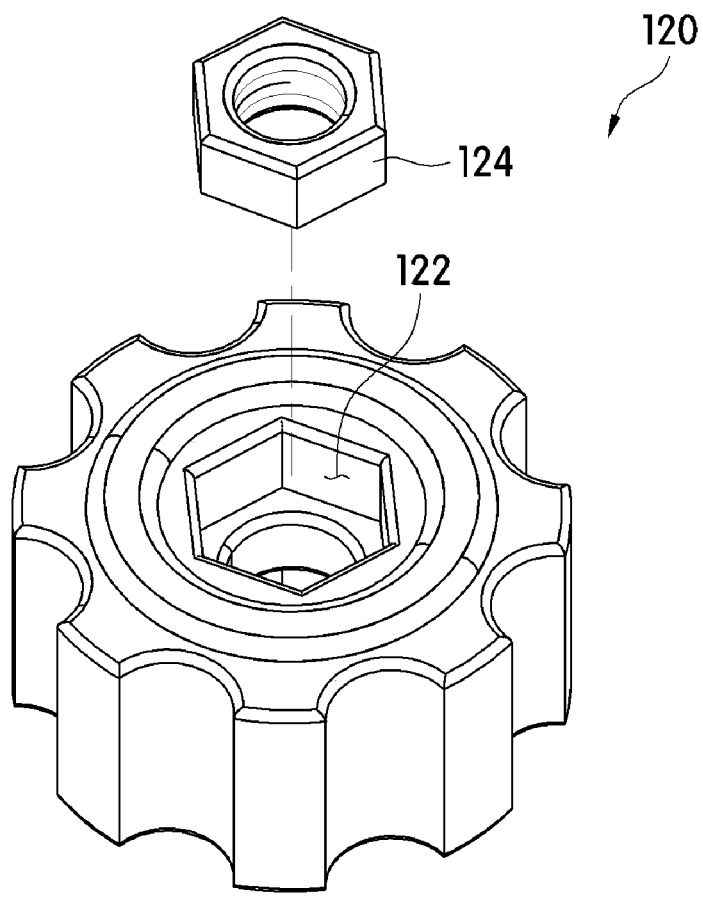
FIG. 5 is an exploded perspective view illustrating a rotating member and a coupling member of the cervical brace according to one embodiment of the present invention.
Figure 6:
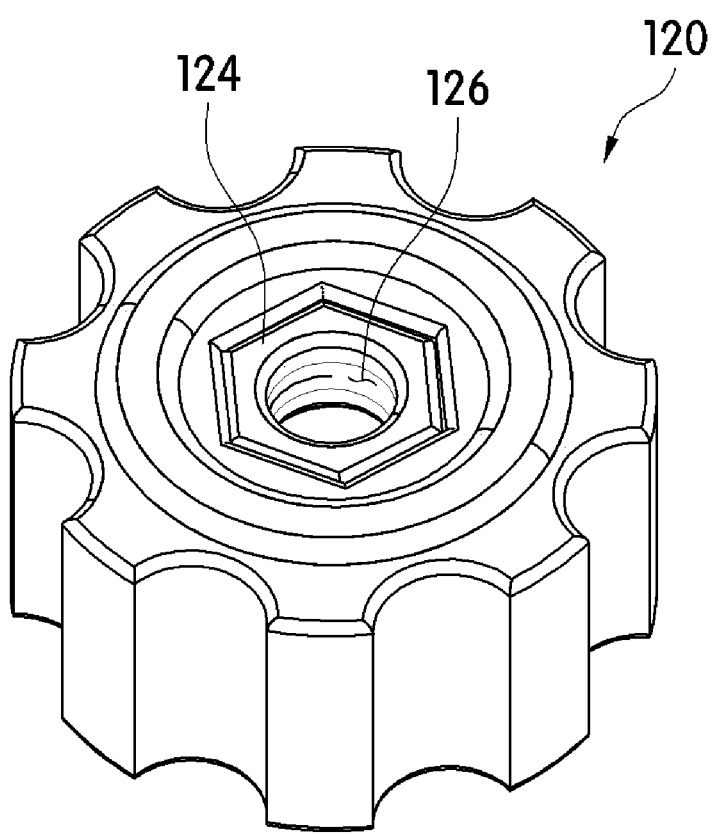
FIG. 6 is a coupling perspective view in FIG. 5.

FIG. 3 is a perspective view illustrating a height adjuster of the cervical brace according to one embodiment of the present invention, FIG. 4 is an exploded perspective view in FIG. 3, FIG. 5 is an exploded perspective view illustrating a rotating member and a coupling member of the cervical brace according to one embodiment of the present invention, and FIG. 6 is a coupling perspective view in FIG. 5.

As illustrated in FIG. 3, the height adjusters 100 are installed for adjusting a height between the lower support 20 and the upper support 10 so that the cervical brace 1 may fit the wearer's body shape.

The height adjusters 100 may each include a body 110 installed on one side surface of the upper support 10, a rotating member 120 rotatable in both directions and positioned at one side of the body 110, the connecting member 130 fixedly coupled to the support member 22 of the lower support 20 corresponding to the rotating member 120 and installed to penetrate through the rotating member 120.

As illustrated in FIG. 4, an accommodation portion 112 having one open side to accommodate the rotating member 120 may be formed at the body 110.

Specifically, the body 110 may be formed in a "C" shape to be in contact with upper and lower surfaces of the rotating member 120. Specifically, the body 110 has an upper beam protruding from an upper end to one side and a lower beam protruding from a lower end to one side. Accordingly, the accommodating portion 112 is formed between the upper beam and the lower beam.

In addition, a pair of through holes 114 may be formed in the body 110 in contact with the upper and lower surfaces of the rotating member 120. That is, the pair of through holes 114 may be formed at upper and lower portions of the accommodation portion 112 of the body 110. Specifically, a pair of through holes 114 may be formed in the upper beam and the lower beam, respectively.

Meanwhile, although the body 110 is illustrated and described to have a "C" shape, the configuration of the present invention is not limited thereto. For example, the body may be freely formed in any shape as long as a part of the body 110 is opened so that the wearer may rotate the rotating member.

The rotating member 120 is for vertically moving the upper support 10 along the connecting member 130, and may rotate about the connecting member 130 in both directions.

Specifically, as illustrated in FIG. 3, the rotating member 120 may be accommodated in the accommodation portion 112, and may be formed in a cylindrical shape with an upper surface in contact with a lower surface of the upper beam and a lower surface in contact with an upper surface of the lower beam, and may be formed such that one side of a circumferential surface is disposed outside a front end of the upper beam and a front end of the lower beam, and as illustrated in FIG. 5, seating grooves 122 may be formed in the upper and lower surfaces of the rotating member 120. As illustrated in FIG. 3, an upper guide protrusion may protrude from the upper surface of the rotating member 120 in the shape of a ring through which the connecting rod 130 passed through the center. An upper guide groove is recessed in the shape of a ring on the lower surface of the upper beam so that the upper guide protrusion is inserted. A lower guide protrusion may protrude from the lower surface of the rotating member in the shape of a ring through which the connecting rod 130 passed through the center. A lower guide groove is recessed in the shape of a ring on the upper surface of the lower beam so that the lower guide protrusion is inserted.

As illustrated in FIG. 6, coupling members 124 are seated in the pair of seating grooves 122. The pair of seating grooves 122 may be formed in the upper and lower surfaces of the rotating member 120 corresponding to the through holes 114 formed at upper and lower portions of the accommodation portion 112.

In addition, the seating grooves 122 may be formed in a shape corresponding to a shape of the coupling member 124, and a nut may be used as the coupling member 124.

Here, a central through hole 126 through which the connecting member 130 may penetrate may be formed at the center of the seating grooves 122 and the center of the coupling members 124.

The connecting portion 130 in a cylindrical shape may include one end coupled to the support member 22 and formed to extend toward the upper support 10, and include a circumferential surface having a screw thread to be coupled to the coupling member 124.

Here, the connecting member 130 may be formed to have a predetermined length, and specifically, the predetermined length of the connecting member 130 may be greater than a length between a bottom surface of the support member 22 of the lower support 20 and the height adjuster 110 of the upper support 10.

In addition, the connecting member 130 may be installed to penetrate one surface of the lower support 20 corresponding to the rotating member 120 and the rotating member 120.

Specifically, one side of the connecting member 130 may be fixed to an upper portion of the support member 22 installed at one surface of the lower support 20, and the other side of the connecting member 130 may be installed to penetrate the pair of through holes 114 formed in the accommodation portion 112 and the central through hole 126. The rotating member 120 may be penetrated by the connecting rod together with the upper beam and the lower beam so as to rotate in both directions about the axis of the connecting rod 130.

That is, the connecting member 130 coupled to the support member 22 of the lower support 20 may sequentially penetrate the through hole 114 formed in the lower portion of the accommodation portion 112 of the body 110, the central hole 126 of the rotating member 120, and the through hole 114 formed in the upper portion of the accommodation portion 112 of the body 110.

A method of adjusting a height of the upper support 10 having the above-described structure will be simply described as follows. As illustrated in FIG. 3, when a wearer rotates the rotating member 120, the pair of coupling members 124 seated on the upper and lower surfaces of the rotating member 120 may move along the screw thread of the connecting member 130.

Specifically, when the wearer rotates the rotating member 120 rotatable in both directions in one direction (see an arrow A), the coupling members 124 seated in the seating groove 122 of the rotating member 120 may rise along the connecting member 130, and accordingly, the upper support 10 may rise (see an arrow B)

On the other hand, when the rotating member 120 is rotated in the other direction, the coupling members 124 seated in the seating groove 122 of the rotating member 120 may be lowered along the connecting member 130, and accordingly, the upper support 10 may be lowered.

Accordingly, the wearer may adjust a position of the upper support 10 with respect to the lower support 20 to fit his or her jaw.

The body 110 of the height adjuster 100 having the above-described structure may be installed to be detachable from the upper support 10, and the fixing member 140 to which the body 110 is fixedly coupled may be installed at the upper support 10.

Specifically, the above will be described below with reference to FIGS. 7 to 11.

Figure 7:
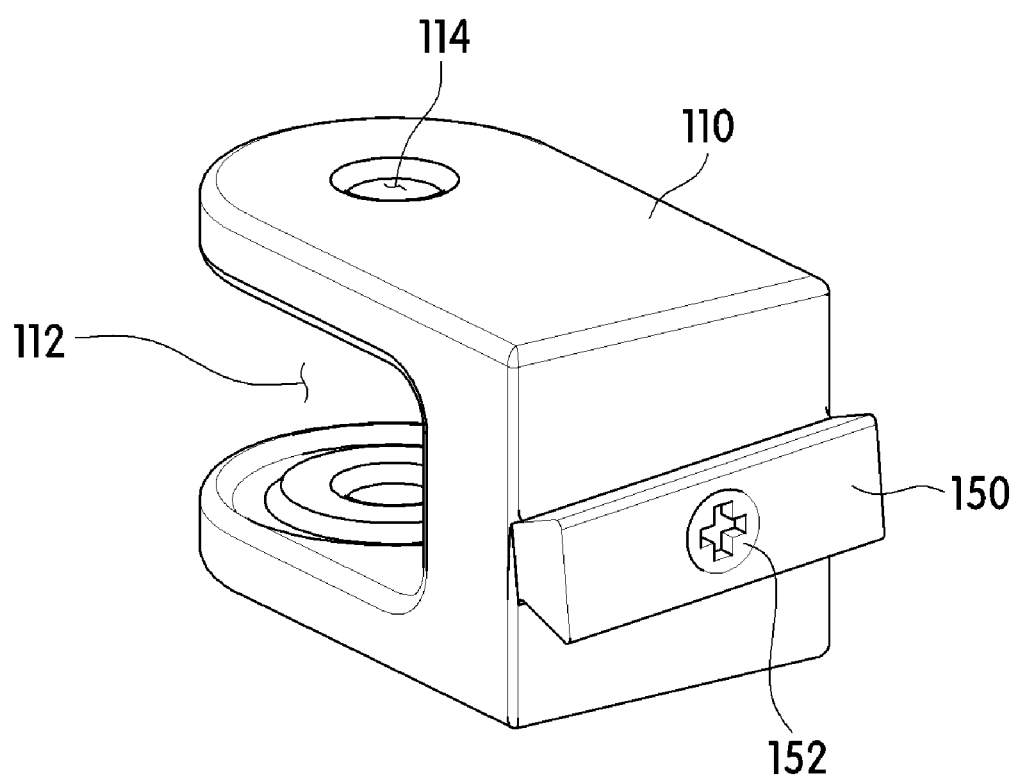
FIG. 7 is a view illustrating an angle adjusting member of the cervical brace according to one embodiment of the present invention.
Figure 8:
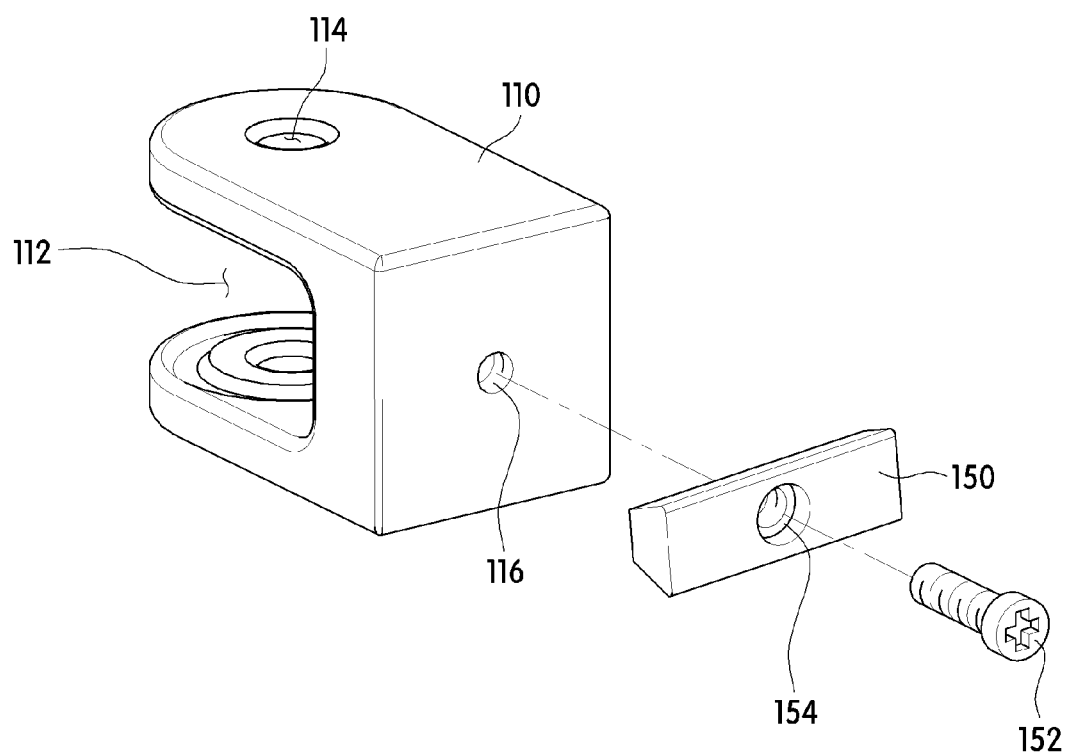
FIG. 8 is an exploded perspective view in FIG. 7.
Figure 9:
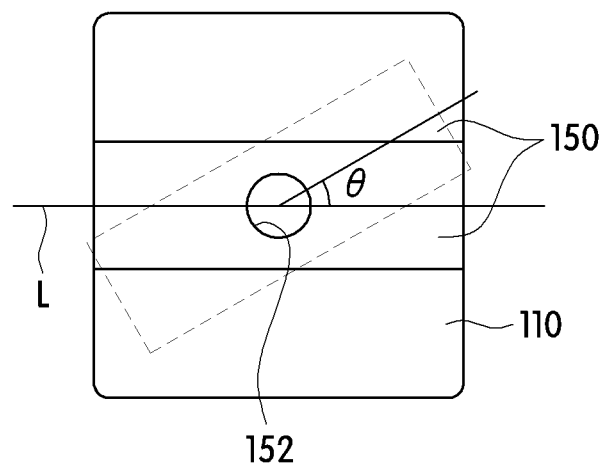
FIG. 9 is a cross-sectional view illustrating a method of operating the angle adjusting member shown in FIG. 8.
Figure 10:
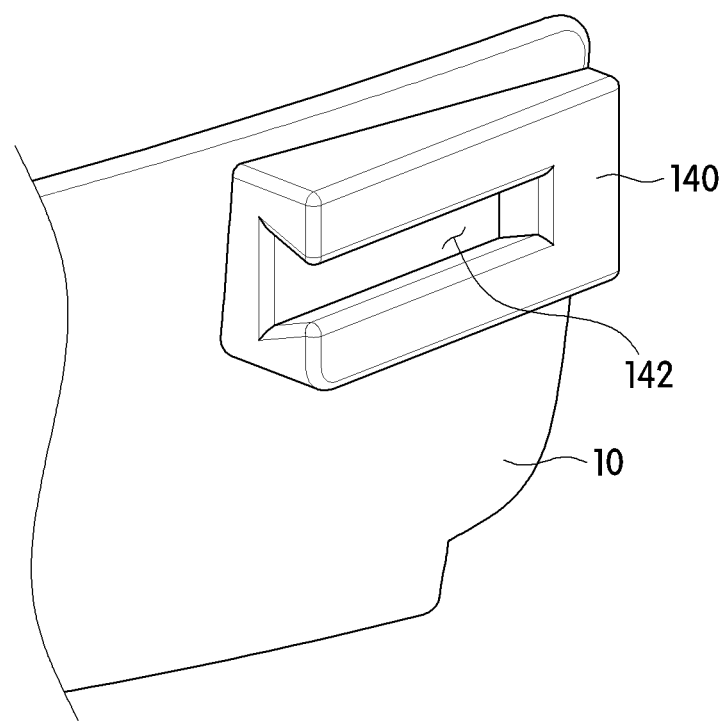
FIG. 10 is a perspective view illustrating a fixing member of the cervical brace according to one embodiment of the present invention.
Figure 11:
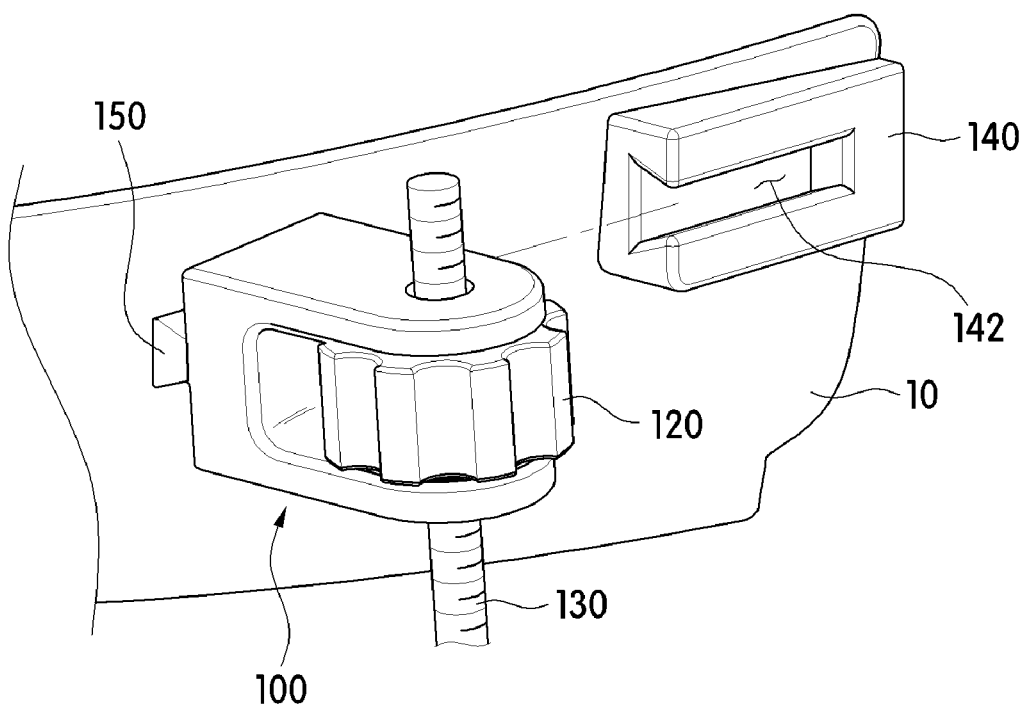
FIG. 11 is a view illustrating a state in which the angle adjusting member is inserted into the fixing member of the cervical brace according to one embodiment of the present invention.

FIG. 7 is a view illustrating an angle adjusting member of the cervical brace according to one embodiment of the present invention, FIG. 8 is an exploded perspective view in FIG. 7, FIG. 9 is a cross-sectional view illustrating a method of operating the angle adjusting member shown in FIG. 8, FIG. 10 is a perspective view illustrating a fixing member of the cervical brace according to one embodiment of the present invention, and FIG. 11 is a view illustrating a state in which the angle adjusting member is inserted into the fixing member of the cervical brace according to one embodiment of the present invention.

As illustrated in FIG. 7, an angle adjusting member 150 configured to adjust an angle of the upper support 10 to the wearer's jaw may be detachably installed at the other side of the body 110.

The angle adjusting member 150 may have a trapezoidal cross-section, and be screwed to the other side of the body 110.

That is, the angle adjusting member 150 may be formed so that the cross-sectional area thereof gradually increases from one surface of the angle adjusting member 150 toward the outside.

Specifically, as illustrated in FIG. 8, a hole 154 through which a screw 152 may penetrate may be formed in the angle adjusting member 150, and a coupling groove 116 into which a screw of thread of the screw 152 is inserted and coupled may be formed at the other side of the body 110 corresponding to the hole 154.

As illustrated in FIG. 9, the angle adjusting member 150 may be inclined at a rotation angle θ by being rotated about the horizontal line L perpendicular to the direction of gravity.

In addition, the angle adjusting member 150 may be pressed against and fixed to the body 110 in a state in which the angle adjusting member 150 is inclined at a rotation angle.

In addition, as illustrated in FIG. 10, the angle adjusting member 150 inclined at a rotation angle may slide and be fixed to the fixing member 140 installed at the upper support 10.

Here, a guide groove 142 in a shape corresponding to a shape of the angle adjusting member 150 may be formed in the fixing member 140.

That is, the guide groove 142 may be formed to have a trapezoidal cross-section that is the same as that of the angle adjusting member 150.

A method of adjusting an angle of the upper support 10 of the cervical brace 1 having the above-described configuration will be described as follows.

As the wearer loosely inserts the angle adjusting member 150 into the coupling groove 116 of the other side of the body 110 using the screw 152, the angle adjusting member 150 may be temporarily fixed to the body 110.

Here, as illustrated in FIG. 9, the angle adjusting member 150 may rotate about the horizontal line L perpendicular to the direction of gravity.

Therefore, after rotating the angle adjusting member 150, the wearer may press and fix the angle adjusting member 150 inclined at a predetermined rotation angle against and to the other side of the body 110 through the screw 152.

Finally, as illustrated in FIG. 11, the angle adjusting member 150 may be fixed by being inserted into the guide groove 142 of the fixing member 140, and accordingly, an angle of the upper support 10 may be adjusted to fit the wearer's body shape through the angle adjusting member 150.

Here, the fixing member 140 may be installed at the upper support 10 parallel to the horizontal line L. As the angle adjusting member 150 inserted into the guide groove 142 of the fixing member 140 is fixed to the body 110 in a state in which the angle adjusting member 150 is inclined with respect to the horizontal line L, the body 110 is inclined at a rotation angle θ of the angle adjusting member 150.

In addition, since the body 110 is inserted into the guide groove 142 of the fixing member 140 in a state in which the body 110 is inclined at a rotation angle θ, the upper support 10 may also be inclined at the rotation angle θ of the angle adjusting member 150.

Accordingly, since a position of the upper support 10 may fit the wearer's body shape, the wearing sensation of the cervical brace 1 may be improved.

In the cervical brace 1 according to the present invention, since the body 110 and the angle adjusting member 150 of the height adjuster 100 are detachable from each other, a height of the upper support 10 may also be adjusted through the rotating member 120 and the connecting member 140 after an angle of the upper support 10 is adjusted through the angle adjusting member 150.

Accordingly, as the height adjusting member connected to the lower support to adjust a height of the upper support and the angle adjusting member are provided at the one side of the upper support supporting the wearer's jaw, the height and angle of the upper support may be easily adjusted to fit the wearer's body shape. Therefore, the wearing sensation the can be improved.

In addition, since the coupling member of the height adjuster is formed in a nut shape, and the connecting member is formed to have the screw thread formed on the circumferential surface to be coupled to the coupling member, the number of parts may be dramatically decreased. Therefore, the manufacturing and assembly cost of products can be decreased.

In addition, since the coupling member of the height adjuster is formed in a nut shape, and the connecting member is formed to have the screw thread formed on the circumferential surface to be coupled to the coupling member, the abrasion phenomena can be prevented.

While embodiments of the present invention have been described above, the scope of the present invention is not limited thereto. Other embodiments may easily be made by those understanding the scope of the present invention and skilled in the art by addition, change, deletion, and the like of components, and these are also included in the range of the scope of the present invention.

What is claimed is:

1. A cervical brace comprising:
    an upper support configured to support and cover a jaw of a wearer;
    a lower support configured to be supported by being pressed against shoulders around a neck of the wearer;
    a rear support positioned behind the upper support and the lower support and configured to support a rear of the neck of the wearer;
    a height adjuster comprising a body installed on one side of the upper support and formed in a "C" shape by having an upper beam protruding to one side from an upper end of the body and a lower beam protruding to the one side from a lower end of the body to form an accommodation portion opened to the one side, a connecting rod in a cylindrical shape extending from one surface of the lower support toward the body and fixed at one surface of the lower support, and a rotating member accommodated in the accommodation portion of the body and formed in a cylindrical shape with an upper surface in contact with a lower surface of the upper beam and a lower surface in contact with an upper surface of the lower beam, and penetrated by the connecting rod together with the upper beam and the lower beam so as to rotate in both directions about an axis of the connecting rod;

an angle adjusting block configured to adjust an angle of the upper support with respect to the jaw of the wearer being detachably installed at another side of the body, coupling members coupled to the connecting rod being disposed at the rotating member through which the connecting rod penetrates, and seating grooves in which the coupling members are seated being formed in the rotating member at which the coupling members are disposed, wherein the seating grooves are formed in the upper surface and the lower surface of the rotating member, and the coupling members are provided in a pair and respectively seated in a pair of seating grooves formed in the upper surface and the lower surface of the rotating member, wherein each of the coupling members has a nut shape, and the connecting rod comprises a screw thread formed on a circumferential surface to be coupled to the coupling members, wherein the seating grooves are formed to correspond to a shape of the coupling members so that the rotating member rotates together with the coupling members, wherein the body of the height adjuster moves upward and downward along the connecting rod according to a rotating direction of the rotating member and thus the upper support moves upward and downward with respect to the lower support, wherein the body of the height adjuster is installed to be detachable from the upper support, and a fixing member to which the body is coupled to be fixed is installed at the upper support, wherein a cross-sectional area of the angle adjusting block gradually increases from one surface of the angle adjusting block toward outside the angle adjusting block, the angle adjusting block is coupled to the fixing member and the angle adjusting block is fixed to the body in a state in which the angle adjusting block is inclined at a rotation angle about a horizontal line or parallel to the horizontal line, and wherein the rotating member formed so that one side of a circumferential surface is disposed outside a front end of the upper beam and a front end of the lower beam.

2. The cervical brace of claim 1, wherein the angle adjusting block is screwed to the body.

3. The cervical brace of claim 1, wherein the angle adjusting block has a section formed in a trapezoidal shape.

4. The cervical brace of claim 2, wherein the fixing member has a guide groove formed in a shape corresponding to the angle adjusting block.

5. The cervical brace of claim 1, further comprising an upper guide protrusion protruding from the upper surface of the rotating member in the shape of a ring having a center through which the connecting rod passes;

an upper guide groove recessed in the shape of a ring on the lower surface of the upper beam so that the upper guide protrusion is inserted;

a lower guide protrusion protruding from the lower surface of the rotating member in the shape of a ring having a center through which the connecting rod passes; and a lower guide groove recessed in the shape of a ring on the upper surface of the lower beam so that the lower guide protrusion is inserted.

6. The cervical brace of claim 1, further comprising a support member to which the connecting rod is fixed being installed at one surface of the lower support.

* * * * *